United States Patent
Chon et al.

(10) Patent No.: US 12,290,281 B2
(45) Date of Patent: May 6, 2025

(54) VALVED CANNULA ASSEMBLY

(71) Applicant: Alcon Inc., Fribourg (CH)

(72) Inventors: James Y. Chon, Irvine, CA (US); Joel Cicchella, Tustin, CA (US); Robert Jeffrey Heng, Costa Mesa, CA (US); Grace Chuang Liao, Irvine, CA (US); Ashish Sinha, Irvine, CA (US)

(73) Assignee: Alcon Inc., Fribourg (CH)

( * ) Notice: Subject to any disclaimer, the term of this patent is extended or adjusted under 35 U.S.C. 154(b) by 340 days.

(21) Appl. No.: 17/811,144

(22) Filed: Jul. 7, 2022

(65) Prior Publication Data

US 2023/0021425 A1 Jan. 26, 2023

Related U.S. Application Data

(60) Provisional application No. 63/223,672, filed on Jul. 20, 2021.

(51) Int. Cl.
*A61B 17/34* (2006.01)
*A61F 9/007* (2006.01)

(52) U.S. Cl.
CPC ...... *A61B 17/3423* (2013.01); *A61B 17/3462* (2013.01); *A61F 9/00727* (2013.01)

(58) Field of Classification Search
CPC ............. A61B 17/3423; A61B 17/3462; A61F 9/00727; A61F 9/00736; A61F 9/007
See application file for complete search history.

(56) References Cited

U.S. PATENT DOCUMENTS

| | | | |
|---|---|---|---|
| 4,033,349 A | 7/1977 | Baehr | |
| 5,817,099 A | 10/1998 | Skolik et al. | |
| 6,045,535 A | 4/2000 | Ben | |
| 6,740,064 B1 | 5/2004 | Sorrentino et al. | |
| 7,783,346 B2 | 8/2010 | Smith et al. | |
| 8,062,260 B2 | 11/2011 | McCawley | |
| 8,277,418 B2 | 10/2012 | Lopez | |
| 8,343,106 B2 | 1/2013 | Alcon | |
| 8,679,064 B2 | 3/2014 | Lopez | |
| 9,730,834 B2 | 8/2017 | Charles | |
| 9,925,326 B2 | 3/2018 | Scheller | |
| 10,905,462 B2 | 2/2021 | Ochoa | |
| 11,166,843 B2 | 11/2021 | Hallen | |
| 11,173,008 B2 | 11/2021 | Mirsepassi et al. | |

(Continued)

FOREIGN PATENT DOCUMENTS

| NL | 2010857 C2 | 11/2014 |
|---|---|---|
| WO | 2008045744 A2 | 4/2008 |

OTHER PUBLICATIONS

Chon, James Y., "Cannula Assembly", U.S. Appl. No. 18/455,809, filed Aug. 25, 2023, 20 pp.

*Primary Examiner* — Richard G Louis

(57) ABSTRACT

Embodiments disclosed herein provide devices, systems, and methods for instrument exchanges during ophthalmic surgery. More particularly, the present disclosure relates to valved cannula assemblies and methods of use thereof. A valved cannula assembly includes a cannula having a head at a proximal end of the cannula and a hollow rod extending from the head to a distal end of the cannula. The valved cannula assembly includes a valved hub coupled to the head and including a septum having two or more curved flaps configured to provide an opening for an instrument.

3 Claims, 8 Drawing Sheets

(56) References Cited

U.S. PATENT DOCUMENTS

| | | |
|---|---|---|
| 11,395,713 B2 | 7/2022 | Grueebler et al. |
| 11,399,914 B2 | 8/2022 | Anderson et al. |
| 2003/0060770 A1* | 3/2003 | Wing ................. A61B 17/3496 604/164.02 |
| 2006/0089526 A1 | 4/2006 | Chen |
| 2008/0097346 A1 | 4/2008 | Charles |
| 2008/0172009 A1 | 7/2008 | Attinger |
| 2008/0177239 A1 | 7/2008 | Li |
| 2008/0312662 A1 | 12/2008 | Hickingbotham |
| 2009/0076463 A1 | 3/2009 | Attinger |
| 2009/0234292 A1 | 9/2009 | Di Nardo |
| 2011/0087170 A1* | 4/2011 | Insignares .......... A61B 17/3462 604/167.03 |
| 2011/0152774 A1* | 6/2011 | Lopez .................... A61F 9/007 604/167.01 |
| 2017/0119491 A1 | 5/2017 | Mirsepassi |
| 2018/0021063 A1* | 1/2018 | Main ................. A61B 17/3474 604/167.01 |
| 2018/0353326 A1 | 12/2018 | Hallen |
| 2019/0046288 A1* | 2/2019 | Anderson .......... A61B 17/3421 |
| 2019/0053825 A1 | 2/2019 | Ochoa |
| 2019/0239979 A1 | 8/2019 | Abt |
| 2019/0374248 A1 | 12/2019 | Grueebler |
| 2019/0374249 A1 | 12/2019 | Abt |
| 2020/0085615 A1 | 3/2020 | Abt |

* cited by examiner

VALVED CANNULA ASSEMBLY

PRIORITY CLAIM

This application claims the benefit of priority of U.S. Provisional Patent Application Ser. No. 63/223,672 titled "VALVED CANNULA ASSEMBLY," filed on Jul. 20, 2021, whose inventors are James Y. Chon, Joel Cicchella, Robert Jeffrey Heng, Grace Chuang Liao and Ashish Sinha, which is hereby incorporated by reference in its entirety as though fully and completely set forth herein.

TECHNICAL FIELD

The present disclosure relates generally to devices, systems, and methods providing an interface for instrument exchanges during ophthalmic surgery. More particularly, the present disclosure relates to valved cannula assemblies and methods of use thereof.

BACKGROUND

Posterior segment surgical procedures are performed to treat conditions of the back of the eye, such as age-related macular degeneration (AMD), diabetic retinopathy and diabetic vitreous hemorrhage, macular hole, retinal detachment, epiretinal membrane, cytomegalovirus (CMV) retinitis, and others.

Certain problems affecting the back of the eye may require a vitrectomy, or surgical removal of the vitreous, which is a normally clear, gel-like substance that fills the center of the eye helping to provide form and shape to the eye. For example, a vitrectomy may be performed to clear blood and debris from the eye, to remove scar tissue, or to alleviate traction on the retina. FIG. 1A is a schematic cross-sectional view of an eye 100 during an exemplary ophthalmic procedure, such as a vitrectomy. To insert valved cannula assembly 110, the tip of a trocar blade, which is detachably coupled to the valved cannula assembly 110, creates a micro-incision in eye wall 102, such as in the pars plana 106. The valved cannula assembly 110 is then fully inserted through the micro-incision in the eye wall 102 made by the trocar blade. After the valved cannula assembly 110 is inserted, the trocar blade is withdrawn through the micro-incision in the eye wall 102, and the valved cannula assembly 110 is left disposed through the eye wall 102. The valved cannula assembly 110 provides an interface for instrument exchanges while, at the same time, providing a self-sealing valve to passively control fluid and pressure communication from inside and outside the eye 100. FIG. 1A shows an example of a valved cannula assembly 110 that is inserted in the eye wall 102, after the trocar blade is withdrawn.

FIG. 1B is an isolated top isometric view of the valved cannula assembly 110 of FIG. 1A. The valved cannula assembly 110 includes a cannula 112 having a distal end configured to extend into the eye 100. Note that, as described herein, a distal end or portion of a component refers to the end or the portion that is closer to a patient's body during use thereof. On the other hand, a proximal end or portion of the component refers to the end or the portion that is distanced further away from the patient's body. In certain cases, the distal end of the cannula 112 has a thickness which resists insertion through the micro-incision created by the trocar blade, sometimes requiring an undesirably high insertion force to be applied to the cannula 112. A valved hub 114 is coupled to a proximal end of the cannula 112 and disposed outside the eye 100 and in contact with an outer surface of the eye wall 102 (shown in FIG. 1A). In certain cases, assembly of the valved cannula assembly 110 can be difficult. During assembly of the valved cannula assembly 110, clocking of the valved hub 114 is needed to precisely align the valved hub 114 with the cannula 112.

A valve septum 116 blocks an opening to a channel 118 (shown in phantom in FIG. 1B) of the valved cannula assembly 110. A slit 120 formed through the valve septum 116 permits access to the channel 118 for regulating fluid and pressure communication to and from the eye 100. In certain cases, the valve septum 116 has a flat top face 122 which is flush with a top face 124 of the valved hub 114. The flat valve septum 116 may resist instrument insertion through the slit 120, sometimes requiring an undesirably high insertion force to be applied to the instrument. The flat valve septum 116 also has the potential to leak when intraocular pressure exceeds ambient pressure. Moreover, the flat top face 122 of the valve septum 116, the top face 122 of the valve septum 116 being at the same level as the top face 124 of the valved hub 114, and translucent appearance of the valve septum 116 sometimes make it difficult to guide instruments to the center of the valve septum 116 complicating instrument insertion.

Therefore, there is a need for improved devices, systems, and methods providing an interface for instrument exchanges during ophthalmic surgery, and there is a particular need for improved valved cannula assemblies and methods of use thereof, which address at least some of the drawbacks described above.

BRIEF SUMMARY

The present disclosure relates generally to devices, systems, and methods providing an interface for instrument exchanges during ophthalmic surgery. More particularly, the present disclosure relates to valved cannula assemblies and methods of use thereof.

In certain embodiments, a valved cannula assembly includes a cannula having a head at a proximal end of the cannula and a hollow rod extending from the head to a distal end of the cannula. The valved cannula assembly includes a valved hub coupled to the head and including a septum having two or more curved flaps configured to provide an opening for an instrument.

In certain embodiments, a cannula includes a head at a proximal end of the cannula and a hollow rod extending from the head to a distal end of the cannula. A wall of the hollow rod has a first thickness at the distal end of the cannula less than a second thickness of remaining portions of the hollow rod.

In certain embodiments, a valved cannula assembly includes a cannula having a head at a proximal end of the cannula and a hollow rod extending from the head to a distal end of the cannula. The valved cannula assembly includes a valved hub coupled to the head of the cannula. The valved hub includes a housing and a valve disposed in the housing. The head of the cannula surrounds at least a portion of an outer surface of the housing of the valved hub.

The following description and the related drawings set forth in detail certain illustrative features of one or more embodiments.

BRIEF DESCRIPTION OF THE DRAWINGS

The appended figures depict certain aspects of one or more disclosed embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Embodiments disclosed herein provide improved devices, systems, and methods for instrument exchanges during ophthalmic surgery.

For example, certain embodiments herein disclose cannulas that have a thin wall section at the distal end of the cannula, in contrast to conventional cannulas which have a greater wall thickness at the distal end. A greater wall thickness corresponds to a higher amount of insertion resistance when inserting a valved cannula assembly through a micro-incision, as compared to a thinner wall thickness. Therefore, in such certain embodiments, the cannulas require less insertion force to be applied to the cannula, thereby increasing the ease of use and also reducing potential for damage to the eye wall.

Further, certain embodiments herein disclose valved cannula assemblies disclosed that are assembled by press-fitting the valved hub onto the cannula, in contrast to conventional valved cannula assemblies in which clocking of the valved hub is needed to precisely align the valved hub with the cannula. Therefore, in such certain embodiments, the valved cannula assemblies are simpler to assemble.

Additionally, certain embodiments herein disclose valved hubs that have a curved septum, in contrast to conventional valved hubs which have a flat septum. Therefore, in such certain embodiments, the valved hubs require less insertion force to be applied to the instrument to pass through the septum and are more resistant to leaking. Furthermore, certain embodiments herein disclose valved hubs that have a septum which is recessed from the top face of the valved hub, in contrast to conventional valved hubs in which the septum is flush with the top face. In such certain embodiments, the valve hubs have a septum which provides a visual contrast with remaining portions of the valved hub, in contrast to conventional valved hubs which have a translucent septum. Therefore, in such certain embodiments, the valved hubs help physically and visually guide instruments to the center of the septum making instrument insertion easier.

Figure 1A:
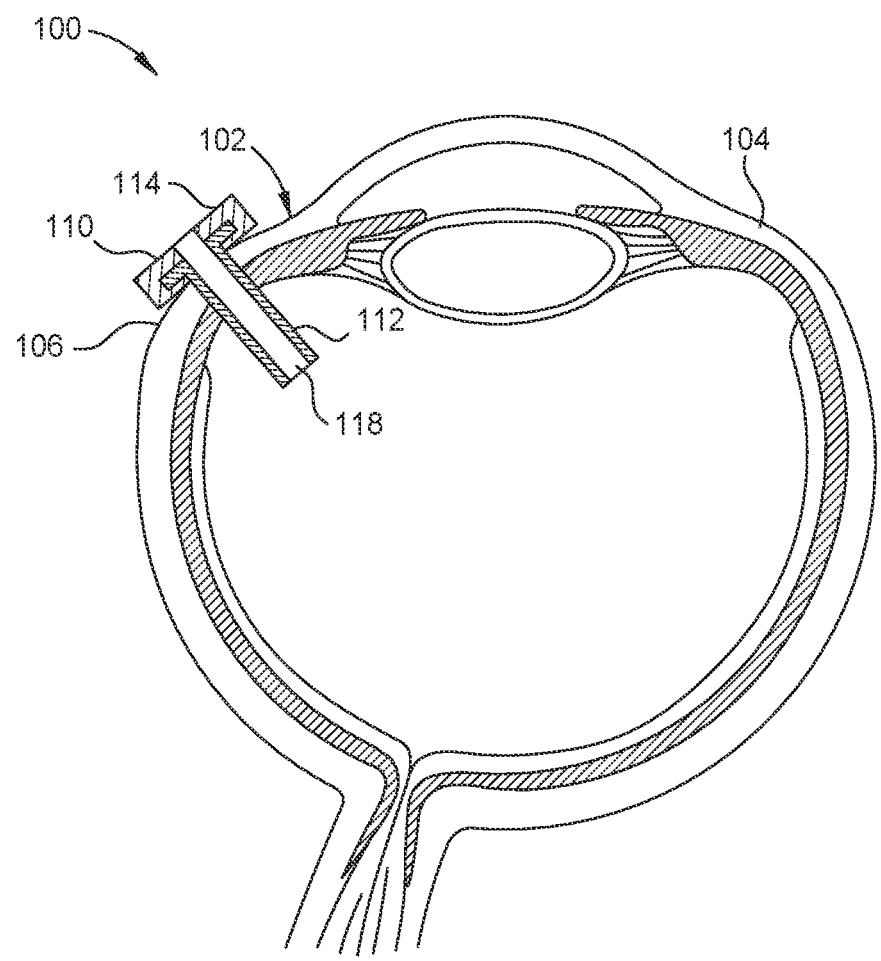
FIG. 1A is a prior art schematic cross-sectional view of an eye during an exemplary ophthalmic procedure.
Figure 1B:
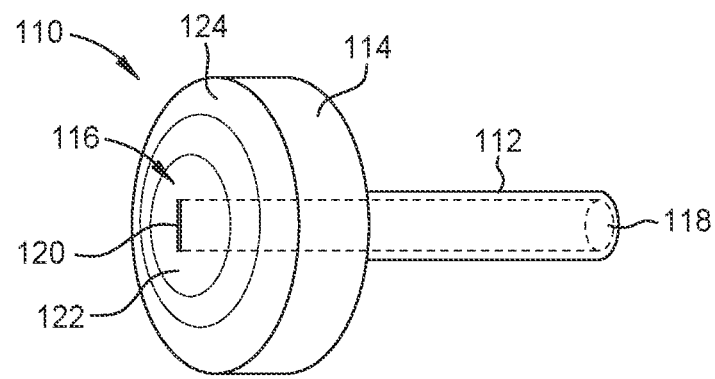
FIG. 1B is an isolated top isometric view of a valved cannula assembly of FIG. 1A.
Figure 2A:
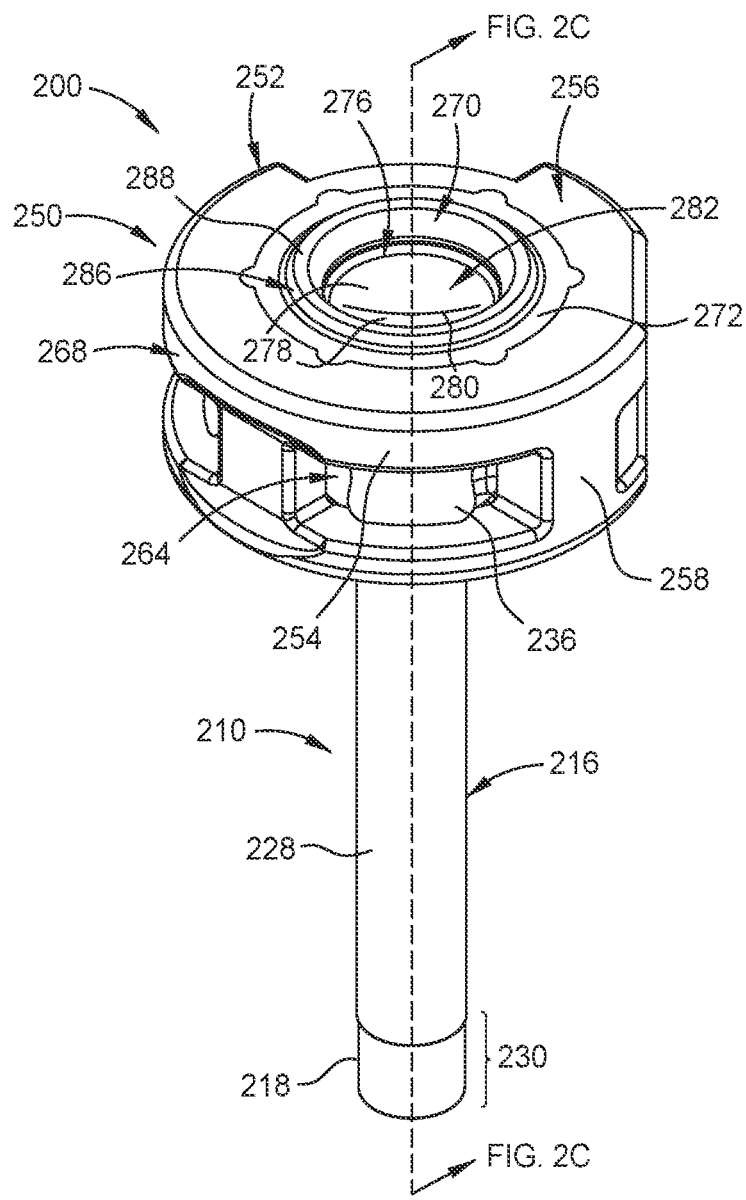
FIGS. 2A-2B are assembled and exploded top isometric views, respectively, of an exemplary valved cannula assembly, in accordance with certain embodiments of the present disclosure.
Figure 2B:
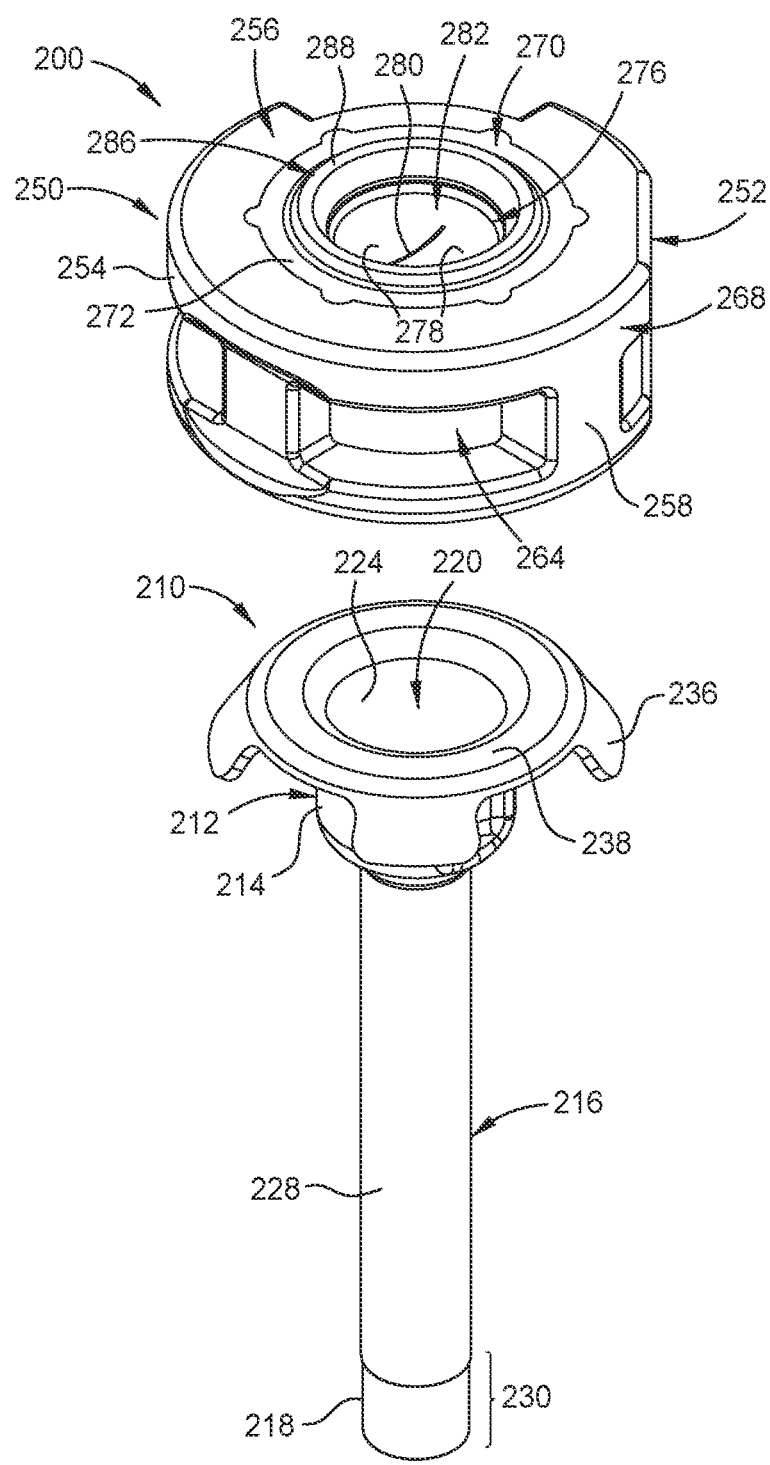
Figure 2C:
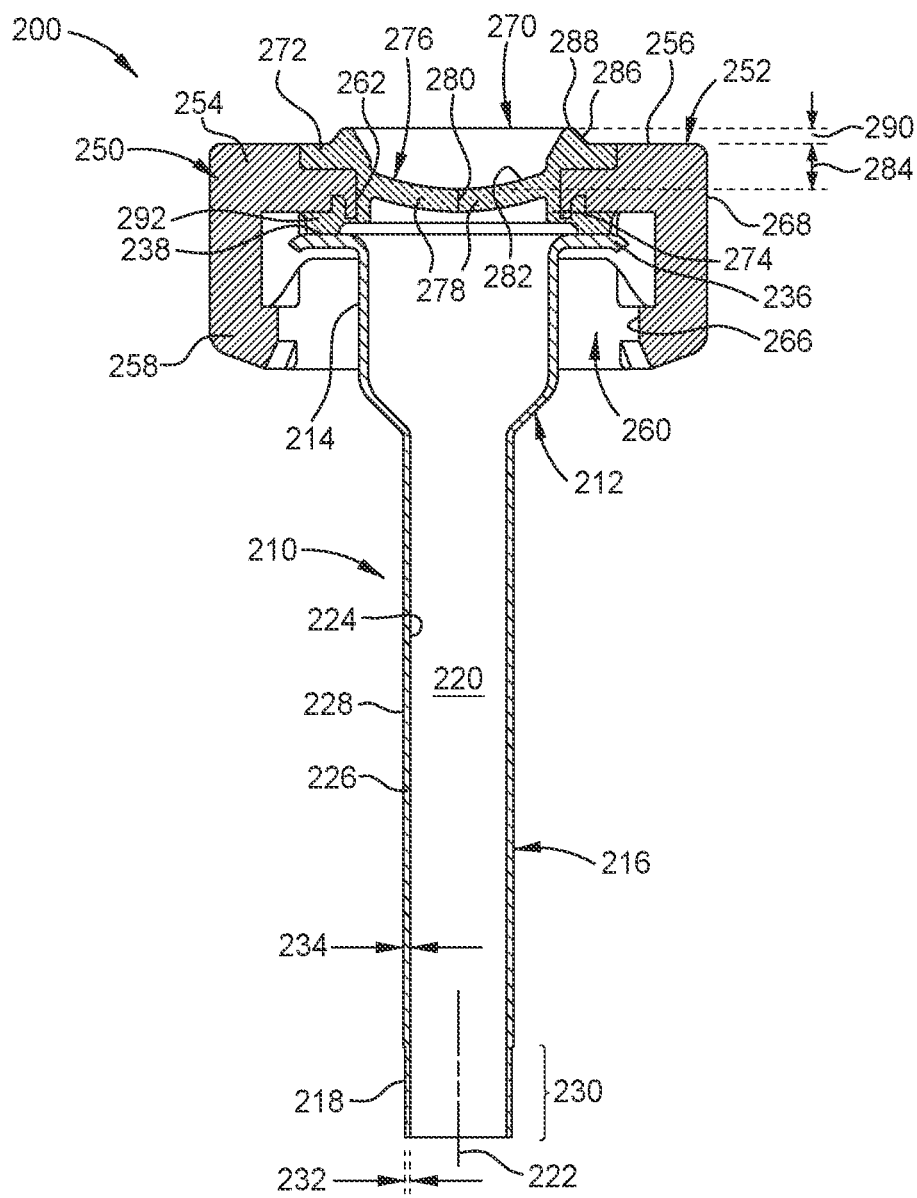
FIG. 2C is a cross-sectional view of the assembled valved cannula assembly of FIG. 2A.

FIGS. 2A-2B are assembled and exploded top isometric views, respectively, of an exemplary valved cannula assembly 200. FIG. 2C is a cross-sectional view of the assembled valved cannula assembly 200 of FIG. 2A. FIGS. 2A-2C are, therefore, described together herein for clarity. The valved cannula assembly 200 generally includes a cannula 210 and a valved hub 250 coupled to the cannula 210. The cannula 210 includes a head 212 at a proximal end 214 of the cannula 210 and a hollow rod 216 extending from the head 212 to a distal end 218 of the cannula 210. Together, the head 212 and the hollow rod 216 form a working channel through which various instruments can be inserted. In certain embodiments, the head 212 has an inner diameter that tapers down to match a smaller inner diameter of the hollow rod 216, for example to help guide an instrument into the hollow rod 216.

In the example of FIGS. 2A-2C, one or more wings 236 extend radially outward from the head 212. When the valved cannula assembly 200 is assembled, the head 212 is disposed inside the valved hub 250, and the one or more wings 236 are disposed through corresponding windows 264 in the valved hub 250 to couple the valved hub 250 to the head 212. Also, when assembled, a top face 238 of the head 212 contacts a downward-facing annular seal 292 disposed in the valved hub 250 to effect an air- and fluid-tight seal between the cannula 210 and the valved hub 250.

The cannula 210 has a channel 220 formed along a longitudinal axis 222 from the proximal end 214 to the distal end 218 of the cannula 210. The channel 220 enables instrument insertion and fluid flow through the cannula 210. A wall 226 of the cannula 210 has an inner surface 224 surrounding the channel 220. A thickness of the wall 226 is measured radially from the inner surface 224 to an outer surface 228 of the wall 226. The cannula 210 has a thin-wall section 230 at the distal end 218. The thin-wall section 230 is thinner compared to the distal end of conventional cannulas. Therefore, the thin-wall section 230 reduces the insertion force needed to insert the cannula 210 through the eye wall 102, which reduces potential for damage to the eye wall 102.

In certain embodiments, a length of the thin-wall section 230 measured along the longitudinal axis 222 may be up to about 20% of a total length of the cannula 210, such as about 5% to about 15%, such as about 10%. A wall thickness 232 of the thin-wall section 230 is less than a wall thickness 234 of remaining portions of the cannula 210 (including remaining portions of the hollow rod 216 above the thin-wall section 230). It is contemplated that the wall thickness 232 may be about 0.0015 inches or less, such as about 0.0009 inches to about 0.0013 inches, such as about 0.0011 inches. In certain embodiments, the wall thickness 232 may be up to about 40% less than the wall thickness 234, such as about 10% to about 40% less, such as about 25% less. The inner surface 224 of the wall 226 above the thin-wall section 230 is flush with the inner surface 224 along the thin-wall section 230. The outer surface 228 of the wall 226 along the thin-wall section 230 is recessed relative to the outer surface 228 above the thin-wall section 230. In some other embodiments, the inner surface 224 of the wall 226 along the thin-wall section 230 may be recessed relative to the inner surface 224 above the thin-wall section 230. In some other embodiments, both the inner and outer surfaces 224, 228 may be recessed in the thin-wall section 230.

The valved hub 250 generally includes a housing 252 and a valve 270. When the valved cannula assembly 200 is assembled, the housing 252 partially and radially surrounds the head 212 of cannula 210. In general, the housing 252 has a cylindrical body with a top portion 254 (including top face 256) and a cylindrical sidewall 258. The housing 252 has an opening 260 in the bottom to receive the head 212 of the cannula 210 and a smaller opening 262 in the top portion 254 to receive the valve 270. The housing 252 includes one or more windows 264 formed in the cylindrical sidewall 258. The windows 264 are configured to receive the one or more wings 236 of the cannula 210 as described above. In certain embodiments, the housing 252 is formed by injection molding. In certain embodiments, the housing 252 comprises a rigid polymer or plastic material, such as polycarbonate or polypropylene.

The valve 270 is disposed in the housing 252. In general, the valve 270 has a cylindrical body with top flange 272 and a cylindrical sidewall 274. The shape of the valve 270 conforms to the profile of the top portion 254 of the housing 252 (including the shape of the opening 260). The valve 270 has a septum 276 with two or more curved flaps 278 configured to provide an opening 280 for an instrument. The septum 276 has a concave shape in relation to the top face 256 of the housing 252. In certain embodiments, a depth of the concave shape measured as a difference between highest and lowest points along a top face 282 of the septum 276 is about 0.003 inches to about 0.005 inches, such as about 0.004 inches. In contrast to conventional valved hubs which have a flat septum, the curved flaps 278 and concave shape of the septum 276 reduce the insertion force needed to insert an instrument through the opening 280, thereby, making instrument insertion easier. In addition, the curved flaps 278 make the septum 276 more resistant to leaking compared to the conventional flat septum.

The top face 282 of the septum 276 is recessed by a distance 284 from the top face 256 of the housing 252. The distance 284 is measured from the top face 256 of the housing 252 to the top face 282 of the septum 276 at a radial center of the septum 276 along the longitudinal axis 222. The distance 284 may be about 0.005 inches or greater, such as about 0.005 inches to about 0.02 inches, such as about 0.01 inches. In contrast to conventional valved hubs in which the septum is flush with the top face, the recessed septum 276 of the valved hub 250 helps physically guide instruments to the opening 280 at the center of the septum 276 making instrument insertion easier.

A raised ring 286 extends upward from the top flange 272 of the valve 270. The raised ring 286 has an upper edge 288 which extends beyond the top face 256 of the housing 252. The raised ring 286 results in the top face 282 of the septum 276 being recessed by a distance 290 from the upper edge 288, where the distance 290 is greater than the distance 284. The distance 290 is measured from the upper edge 288 to the top face 282 of the septum 276 at the radial center of the septum 276 along the longitudinal axis 222. The distance 290 may be about 0.009 inches or greater, such as about 0.009 inches to about 0.024 inches, such as about 0.014 inches.

The annular seal 292 is disposed on a lower surface of the top portion 254 of the housing 252. The seal 292 is disposed inside the inner surface 266 of the cylindrical sidewall 258 for contacting the head 212 of the cannula 210 which, in this example, fits inside the inner surface 266 of the cylindrical sidewall 258 when the valved cannula assembly 200 is assembled as shown in FIG. 2C. The seal 292 contacts the top face 238 of the head 212 when the valved cannula assembly 200 is assembled. In the example of FIGS. 2A-2C, the seal 292 is integral with the valve 270. In some other embodiments, the seal 292 is formed separately from the valve 270 and overmolded onto or coupled to the housing 252.

In certain embodiments, the valve 270 comprises an elastic polymer, such as silicone. The material of the valve 270 is configured to help maintain an intraocular pressure of about 10 mmHg (millimeters of mercury) to about 25 mmHg. In certain embodiments, the valve 270 is overmolded onto the housing 252. In some other embodiments, the valve 270 is formed separately from and subsequently coupled together with the housing 252.

In certain embodiments, the color of the housing 252 is different from the color of the valve 270 to provide a visual contrast between the housing 252 and the valve 270. For example, the housing 252 may be non-colored, such as the color of natural polycarbonate, whereas the valve 270 may be colored. In certain embodiments, the housing 252 may have a more translucent appearance than the valve 270. Compared to conventional valved hubs which have a translucent septum, the visual contrast provided by the color of the valve 270 helps provide visual guidance to the opening 280 at the center of the septum 276 making instrument insertion easier.

Figure 3A:
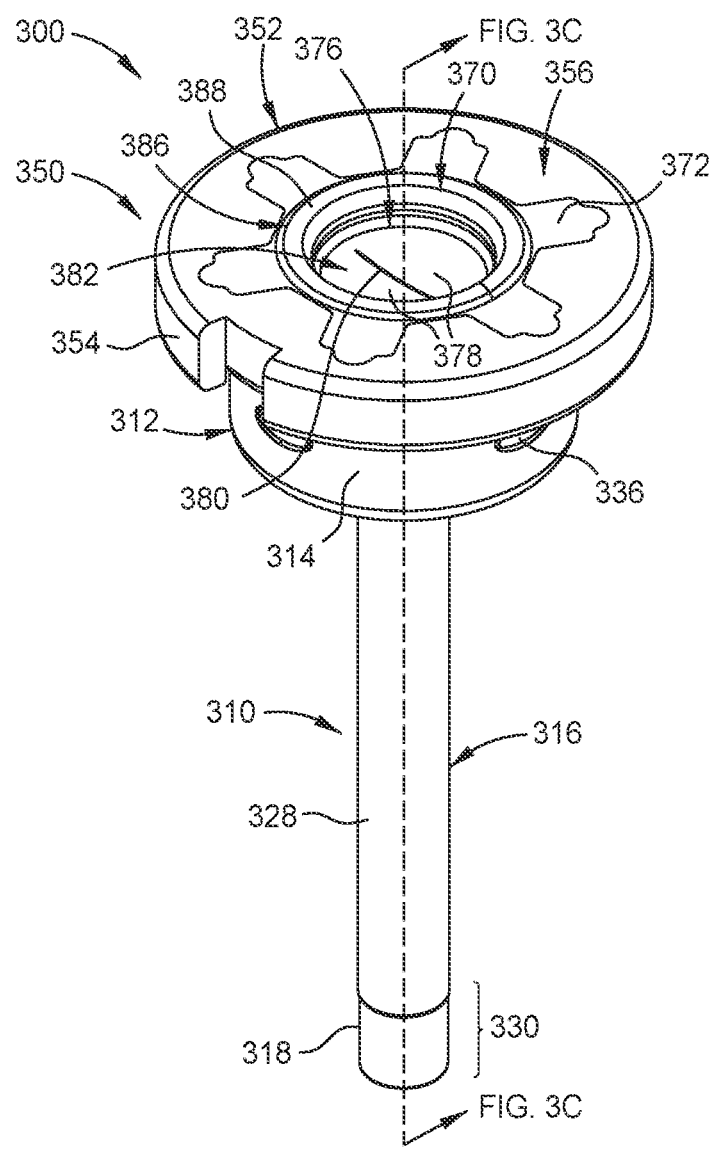
FIGS. 3A-3B are assembled and exploded top isometric views, respectively, of another exemplary valved cannula assembly, in accordance with certain embodiments of the present disclosure.
Figure 3B:
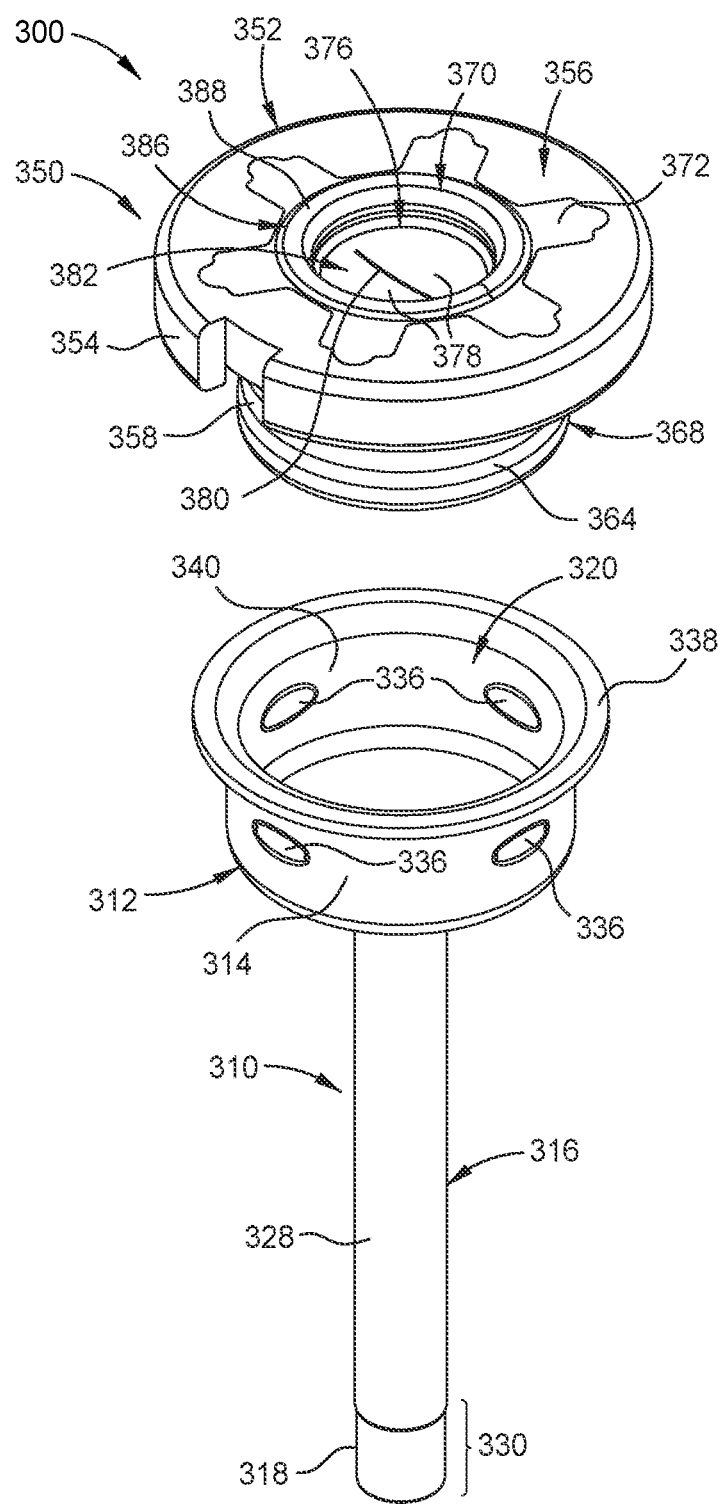
Figure 3C:
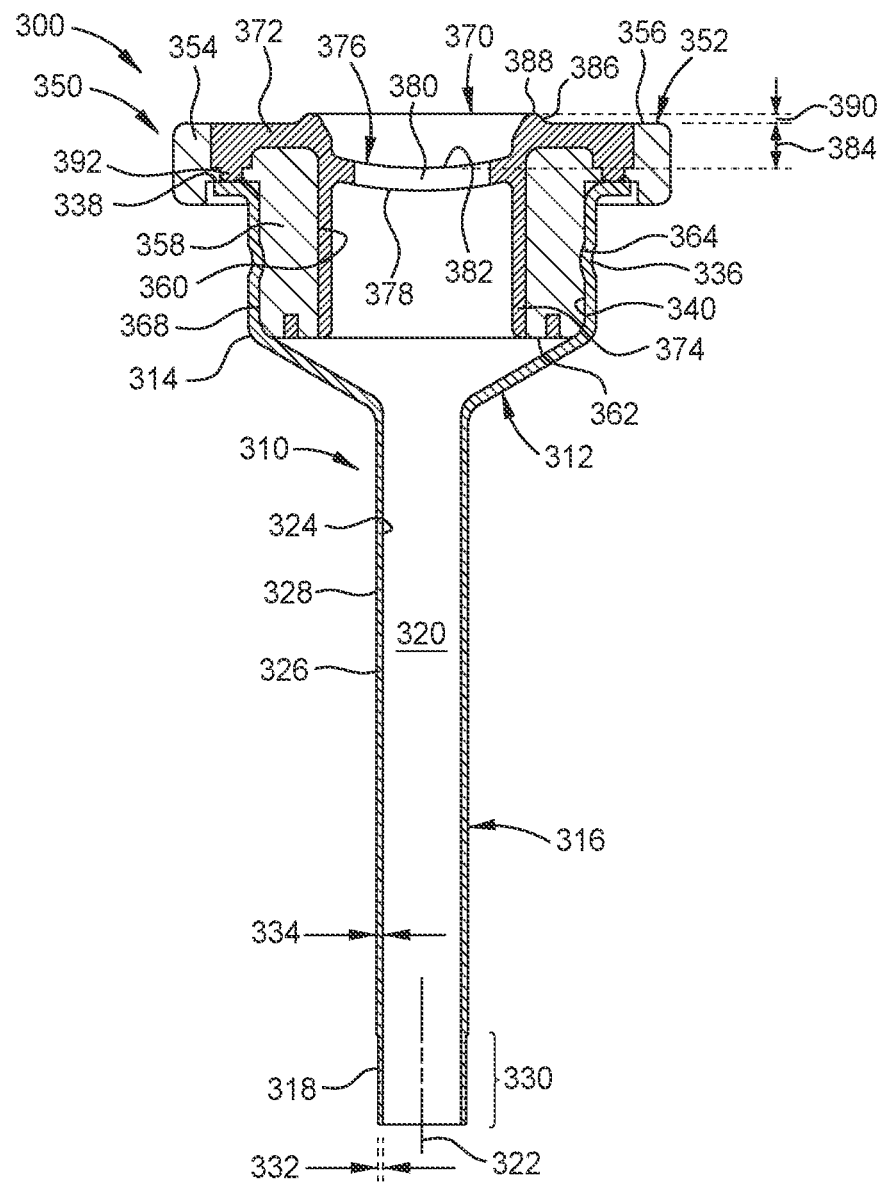
FIG. 3C is a cross-sectional view of the assembled valved cannula assembly of FIG. 3A.

FIGS. 3A-3B are assembled and exploded top isometric views, respectively, of another exemplary valved cannula assembly 300. FIG. 3C is a cross-sectional view of the assembled valved cannula assembly 300 of FIG. 3A. FIGS. 3A-3C are, therefore, described together herein for clarity. The valved cannula assembly 300 is similar to the valved cannula assembly 200 of FIGS. 2A-2C, and aspects of the description thereof may be incorporated herein. The valved cannula assembly 300 generally includes a cannula 310 and a valved hub 350 coupled to the cannula 310. The cannula 310 includes a head 312 at a proximal end 314 of the cannula 310 and a hollow rod 316 extending from the head 312 to a distal end 318 of the cannula 310. Referring to FIG. 3C, the head 312 has an inner diameter greater than the corresponding inner diameter of the head 212 (shown in FIG. 2C). In certain embodiments, the inner diameter of the head 312 tapers down to match a smaller inner diameter of the hollow rod 316, for example to help guide an instrument into the hollow rod 316. The cannula 310 has a thin-wall section 330 at the distal end 318 which is similar to the thin-wall section 230 shown in FIG. 2C, and aspects of the description thereof may be incorporated herein.

In the example of FIGS. 3A-3C, one or more projections 336 extend radially inward from an inner surface 340 of the head 312. When the valved cannula assembly 300 is assembled, the head 312 surrounds at least a portion of the valved hub 350, and the one or more projections 336 are disposed within a corresponding profile 364 in the valved hub 350 to couple the valved hub 350 to the head 312. Also when assembled, a top face 338 of the head 312 contacts a downward-facing annular seal 392 disposed in the valved hub 350 to effect an air- and fluid-tight seal between the cannula 310 and the valved hub 350.

The valved hub 350 generally includes a housing 352 and a valve 370. In the example of FIGS. 3A-3C, when the valved cannula assembly 300 is assembled, the housing 352 is disposed inside the head 312 such that the head 312 surrounds at least a portion of an outer surface of the housing 352. In general, the housing 352 has a cylindrical body with a top portion 354 (including top face 356) and a cylindrical sidewall 358. The housing 352 has a channel 360. In contrast to the example of FIGS. 2A-2C in which the housing 252 has an opening 260 to accommodate the head 212 and a smaller opening 262 to receive the valve 270, the housing 352 has a single continuous channel 360 formed through the top portion 354 and the cylindrical sidewall 358. The channel 360 is aligned with the channel 320 of the cannula 310 and configured to receive the valve 370.

The housing 352 includes a profile 364 formed in an outer surface 368 of the cylindrical sidewall 358. The profile 364 is indented with respect to the outer surface 368 such that an inwardly extending recess is formed in the outer surface 368 for receiving the one or more projections 336 of the cannula 310 as described above. The profile 364 extends substantially 360° circumferentially around the outer surface 368 of the housing 352 of the valved hub 350. In the example of FIGS. 3A-3C, the valved cannula assembly 300 is assembled by press-fitting the valved hub 350 onto the cannula 310, in contrast to conventional valved cannula assemblies in which clocking of the valved hub is needed to precisely align the valved hub with the cannula. Therefore, the valved cannula assembly 300 is simpler to assemble compared to conventional valved cannula assemblies. When the valved cannula assembly 300 is assembled, an interference fit is formed between the inner surface 340 of the head 312 and the outer surface 368 of the housing 352. This interference fit effects an air- and water-tight seal between the cannula 310 and the valved hub 350 in addition to the seal formed by contact between the top face 338 of the head 312 and the seal 392 described above.

The valve 370 is disposed in the housing 352. In general, the valve 370 has a cylindrical body with top flange 372 and a cylindrical sidewall 374. The shape of the valve 370 conforms to the profile of the top portion 354 of the housing 352 (including the shape of the channel 360). In contrast to the valve 270 which is disposed only within the top portion 254 of the housing 252 as shown in FIG. 2C, the cylindrical sidewall 374 of the valve 370 is disposed within the top portion 354 and the cylindrical sidewall 358 and extends continuously from the top face 356 to an opposite bottom face 362 of the housing 352. The septum 376 and raised ring 386 of the valve 370 (including dimensions and recess depths thereof) are similar to the septum 276 and raised ring 286 of the valve 270 shown in FIG. 2C, and aspects of the description thereof may be incorporated herein without limitation.

The annular seal 392 is disposed on a lower surface of the top portion 354 of the housing 352. In contrast to the seal 292 shown in FIG. 2C, the seal 392 is disposed outside the outer surface 368 of the cylindrical sidewall 358 for contacting the head 312 of the cannula 310 which, in this example, fits around the outer surface 368 of the cylindrical sidewall 358 when the valved cannula assembly 300 is assembled as shown in FIG. 3C. The seal 392 contacts the top face 338 of the head 312 when the valved cannula assembly 300 is assembled. In the example of FIGS. 3A-3C, the seal 392 is integral with the valve 370. In some other embodiments, the seal 392 is formed separately from the valve 370 and overmolded onto or coupled to the housing 352.

The materials and fabrication of the valved hub 350 (including the housing 352 and valve 370) are similar to the valved hub 250 of FIGS. 2A-2C, and aspects of the description thereof may be incorporated herein without limitation.

Figure 4:
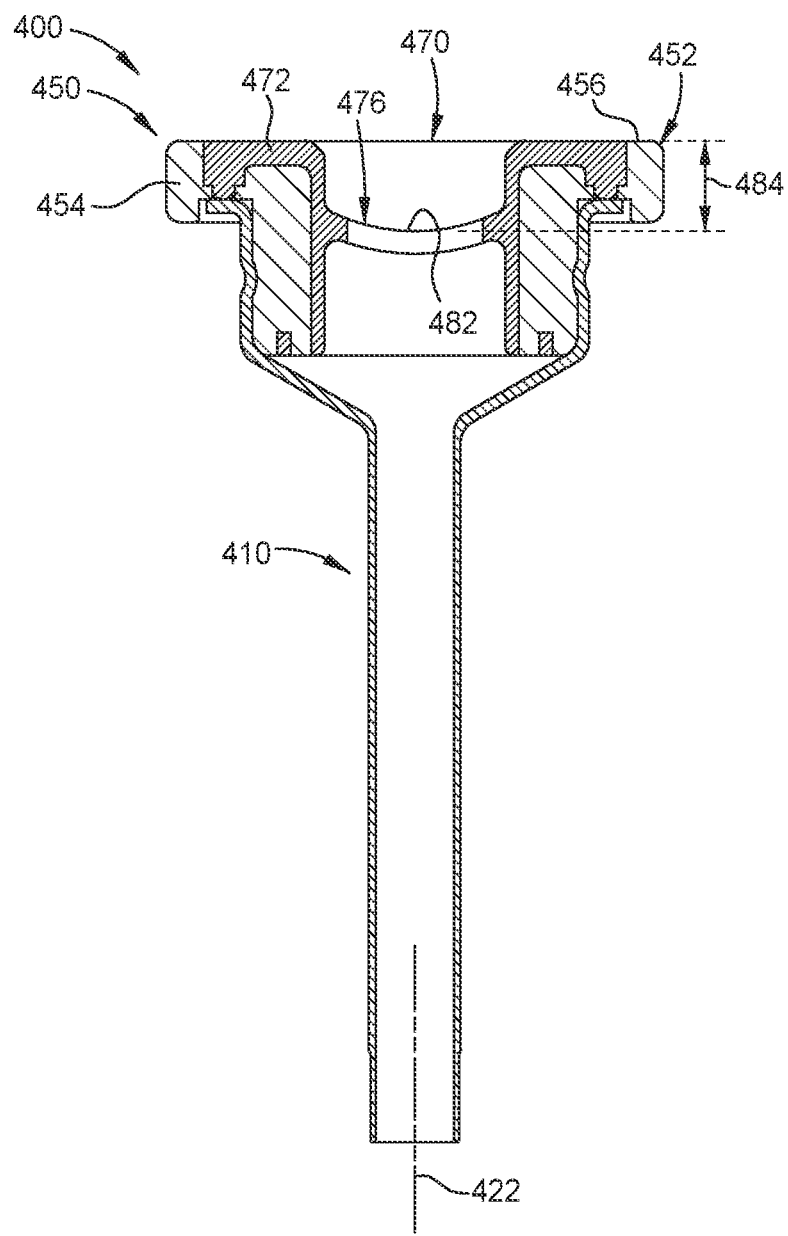
FIG. 4 is a cross-sectional view of yet another valved cannula assembly, in accordance with certain embodiments of the present disclosure.

FIG. 4 is a cross-sectional view of yet another exemplary valved cannula assembly 400. The valved cannula assembly 400 (including the cannula 410 and housing 452 of the valved hub 450) is similar to the valved cannula assembly 300 of FIGS. 3A-3C, and aspects of the description thereof may be incorporated herein without limitation. In contrast to the example of FIGS. 3A-3C, the valved cannula assembly 400 does not have a raised ring extending from the top flange 472 of the valve 470. Instead, the top face 456 of the housing 452 is flush with the top flange 472 of the valve 470. The top face 482 of the septum 476 is recessed by a distance 484 from the top face 456 of the housing 452 measured at a radial center of the septum 476 along the longitudinal axis 422. Without the raised ring extending a recess depth of the septum 476, the distance 484 is greater than the corresponding distance 384 shown in FIG. 3C. For example, the distance 484 may be about 0.01 inches or greater, such as about 0.01 inches to about 0.02 inches, such as about 0.015 inches.

Accordingly, improved devices, systems, and methods are provided for instrument exchanges during ophthalmic surgery.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A valved cannula assembly, comprising:
    a cannula, comprising:
        a head at a proximal end of the cannula; and
        a hollow rod extending from the head to a distal end of the cannula; and
    a valved hub coupled to the head and comprising a septum having two or more curved flaps configured to provide an opening for an instrument;
    wherein a top face of the head contacts a downward facing annular seal disposed in the valved hub to form a seal between the cannula and the valved hub;
    wherein the septum has a concave shape in relation to a top face of the valved hub;
    wherein the septum is recessed from the top face of the valved hub by a distance of about 0.005 inches or greater;
    wherein a wall of the hollow rod has a first thickness at the distal end of the cannula less than a second thickness of remaining portions of the hollow rod;
    wherein the top face of the valved hub comprises a raised ring extending upward from the top face, and wherein the septum is recessed by a first distance from an upper edge of the raised ring greater than a second distance from the top face of the valved hub.

2. The valved cannula assembly of claim 1, wherein the valved hub comprises:
    a housing comprising a first color; and
    a valve disposed in the housing and comprising a second color.

3. The valved cannula assembly of claim 1, wherein the head of the cannula surrounds at least a portion of an outer surface of the valved hub.

* * * * *